United States Patent
Lane et al.

(10) Patent No.: US 7,699,787 B2
(45) Date of Patent: Apr. 20, 2010

(54) MODULAR BLOOD PRESSURE MEASUREMENT APPARATUS

(75) Inventors: John A. Lane, Weedsport, NY (US); Stephen W. Burnett, Locke, NY (US); Thomas J. Grant, Skaneateles, NY (US); Richard W. Newman, Auburn, NY (US); Shawn C. St. Pierre, Syracuse, NY (US); Edward Wright, Raleigh, NC (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 568 days.

(21) Appl. No.: 11/257,714

(22) Filed: Oct. 25, 2005

(65) Prior Publication Data

US 2007/0093718 A1    Apr. 26, 2007

(51) Int. Cl.
*A61B 5/02* (2006.01)
(52) U.S. Cl. .................. 600/490; 600/494; 600/500
(58) Field of Classification Search .............. 600/490, 600/493–496, 500
See application file for complete search history.

(56) References Cited

U.S. PATENT DOCUMENTS

| | | | |
|---|---|---|---|
| 4,493,326 A | 1/1985 | Hill et al. | |
| 4,998,534 A * | 3/1991 | Claxton et al. | 600/483 |
| 5,092,338 A | 3/1992 | Ide et al. | |
| 5,307,263 A | 4/1994 | Brown | |
| 5,687,732 A * | 11/1997 | Inagaki et al. | 600/485 |
| 5,692,512 A | 12/1997 | Flachslaender | |
| 5,711,302 A * | 1/1998 | Lampropoulos et al. | 600/485 |
| 6,050,950 A | 4/2000 | Mohler | |
| 6,068,601 A | 5/2000 | Miyazaki et al. | |
| 6,152,879 A | 11/2000 | Mohler | |
| 6,179,783 B1 | 1/2001 | Mohler | |
| 6,682,508 B1 | 1/2004 | Meythaler et al. | |
| 6,748,250 B1 | 6/2004 | Berman et al. | |
| 2002/0156382 A1 * | 10/2002 | Freund et al. | 600/490 |
| 2002/0198458 A1 | 12/2002 | Tripp, Jr. et al. | |
| 2003/0120164 A1 | 6/2003 | Nielsen et al. | |
| 2003/0176795 A1 | 9/2003 | Harris et al. | |

* cited by examiner

*Primary Examiner*—Charles A Marmor, II
*Assistant Examiner*—Christian Jang

(57) ABSTRACT

A blood pressure measurement apparatus for use in association with a blood pressure measuring cuff includes a housing having an upper shell and a lower shell defining an interior chamber and a replaceable module disposed within the interior chamber. The replaceable module houses a pump for inflating the blood pressure measuring cuff and a vent valve for venting the blood pressure measuring cuff. A cuff pressure sensor is provided within the interior chamber, either within or externally of the replaceable module. A control circuit for controlling the pump and the vent valve is provided on a circuit board disposed externally of the replaceable module. A power pack may be provided within the replaceable module for supplying electric power to the pump, the valve, the control circuit and other components within the interior chamber.

7 Claims, 3 Drawing Sheets

MODULAR BLOOD PRESSURE MEASUREMENT APPARATUS

BACKGROUND OF THE INVENTION

The present invention relates generally to the field of blood pressure measurement and, more particularly, to electronic blood pressure measurement devices.

Electronic blood pressure measurement devices are used in connection with an inflatable sleeve, commonly referred to as a cuff, to measure arterial blood pressure. The cuff, which is adapted to fit around a limb over an artery of a patient, typically around the patient's arm over the brachial artery, includes an interior chamber that is in fluid communication with a motor driven pump for selectively inflating, i.e. pressuring, the interior chamber of the cuff with air. One or more sensors, such as a pressure transducer, are operatively connected in fluid communication with the interior chamber of the cuff for monitoring the air pressure within the interior chamber of the cuff, as well as the patient's blood pressure pulses, as the cuff inflates or deflates. The pressure transducer detects minute changes in the cuff pressure due to flow through the brachial artery. A bleed valve is also operatively connected in fluid communication with the interior chamber to permit selective depressuring of the interior chamber when it is desired to deflate the cuff. Electronic circuitry is provided that processes the signals from the pressure sensing devices and determines the systolic and diastolic blood pressures. Typically, a digital display is also provided for displaying the systolic and diastolic blood pressures. Alternatively, the signals indicative of the systolic and diastolic blood pressure measurements may be transmitted to an external device, such as a laptop or a patient monitor, for display and/or data recording.

U.S. Pat. No. 5,692,512, Flachslaender, discloses a blood pressure measuring device housed in a hermetically sealed, small casing, which is sealed in dust, water and pressure-tight manner by a film on the outside of the casing's cover and on the casing's underside. The device includes a pump, a valve, a pressure sensor and a printed circuit board disposed within the interior of the casing. These components are arranged individually and held on the casing frame by means of conventional snap catches. Housed within the interior of the hermetically sealed casing, these individual components are not readily replaceable in the event of component failure.

Batteries, valves, pumps and pressure sensors, in particular, commonly fail before the other components in an electronic blood pressure measurement device, but have not been easily replaceable or replaced in the field by the end user. Rather, the end user would have to send the complete device back to the manufacturer or authorized service facility for repair or simply discard the device and purchase a new one. A much longer working life for the overall device could be realized if the end user could readily replace the failed component or components in the field. Further, the overall cost to the end user would be reduced if the end user could easily replace the failed components thereby extending the life of the device, rather than purchasing a new device.

SUMMARY OF THE INVENTION

It is an object of one aspect of the invention to provide a blood pressure measurement apparatus having at least one replaceable component module.

It is an object of one aspect of the invention to provide a blood pressure measurement apparatus having a replaceable component module housing at least a motor driven pump and a vent valve.

It is an object of one aspect of the invention to provide a blood pressure measurement apparatus having a replaceable component module housing at least a motor driven pump, a power pack, and a vent valve.

In one aspect of the invention, a blood pressure measurement apparatus for use in pneumatic communication with a blood pressure measuring cuff includes a housing defining an interior chamber and a replaceable component module disposed within the interior chamber. The replaceable component module houses at least a pump for inflating the blood pressure measuring cuff and a vent valve for venting the blood pressure measuring cuff. A cuff pressure sensor is provided within the interior chamber, either within or externally of the replaceable component module. A control circuit is provided for controlling the pump and the vent valve. The blood pressure measurement apparatus may also include a display provided in the housing for displaying a blood pressure reading. A power pack may be provided for supplying electric power to the pump, the valve, the control circuit and other components within the interior chamber. In an embodiment, the replaceable component module houses a pump for inflating the blood pressure measuring cuff, a vent valve for venting the blood pressure measuring cuff, and a power pack.

In another aspect of the invention, a blood pressure measurement apparatus for use in pneumatic communication with a blood pressure measuring cuff includes a housing having an upper casing and a lower casing defining an interior chamber, and a replaceable component module disposed within the interior chamber and detachably mounted to the lower casing of the housing. The upper and lower casings mate to form the housing and define an interior chamber therein. The upper and lower casings are separable for selective opening of the housing for access to the interior chamber for removal and replacement of the replaceable component module. A pump for selectively inflating the blood pressure measuring cuff and a vent valve for selectively venting the blood pressure measuring cuff are housed within the replaceable module. A power pack may be provided within the interior chamber, either externally of or internally within the replaceable component module, for supplying providing electric power to the pump and the valve. A circuit board having a control circuit provided thereon is disposed within the interior chamber and mounted to the upper casing. A pressure sensor is also disposed within the interior chamber and may be mounted to the circuit board. A display may be provided for displaying a blood pressure reading. The display may be disposed in an opening in the upper casing of the housing and connected to the circuit board.

In one embodiment, the blood pressure measurement apparatus includes a housing having an upper casing and a lower casing that mate to form the housing and to define an interior chamber therein, and a replaceable component module disposed within the interior chamber and detachably mounted to the lower casing of the housing. The upper and lower casings are separable for selective opening of the housing for access to the interior chamber for removal and replacement of the replaceable component module. A pump for selectively inflating the blood pressure measuring cuff and a vent valve for selectively venting the blood pressure measuring cuff are housed within the replaceable component module. A circuit board is disposed within the interior chamber and mounted to the upper casing. A pressure sensor for sensing pressure is disposed within the interior chamber and mounted to the circuit board. A display for displaying a blood pressure reading is disposed in an opening in the upper casing of the housing and mounted to the circuit board. A control circuit is provided on the circuit board for controlling the pump, the vent valve, and the display. A power pack is disposed within the interior chamber for providing electric power to the pump, the valve, the pressure sensor, the display and the control circuit. The power pack may be housed within the replaceable component module in operative association with the pump. The control circuit may include a controller for receiving pressure data from the pressure sensor, converting the received pressure data from the pressure sensor to a pressure reading, and providing the pressure reading to the display for display.

In another aspect of the invention, a blood pressure measurement apparatus for use in pneumatic communication with a blood pressure measuring cuff includes a housing defining an interior chamber, a removable pneumatics module and a removable electronics module disposed within the interior chamber. An upper shell and a lower shell mate to form the housing. The interior chamber is accessible by separating the upper and lower shells, thereby permitting selective removal and replacement of either or both of the pneumatics module and the electronics module. The pneumatics module is detachably mounted to the lower shell and includes a pump for selectively inflating the blood pressure measuring cuff and a vent valve for selectively venting the blood pressure measuring cuff. The electronics module is detachably mounted to the upper casing of the housing and includes a display for displaying a blood pressure reading and a control circuit for controlling the pump, the vent valve, and the display. A pressure sensor is provided for sensing cuff pressure. In an embodiment, the pressure sensor is disposed within the electronics module. In an embodiment, the pressure sensor is disposed within the pneumatics module. Further, a power pack may be provided in operative association with the pump, the vent valve, the pressure sensor, the display and the control circuit.

DETAILED DESCRIPTION

Figure 1:
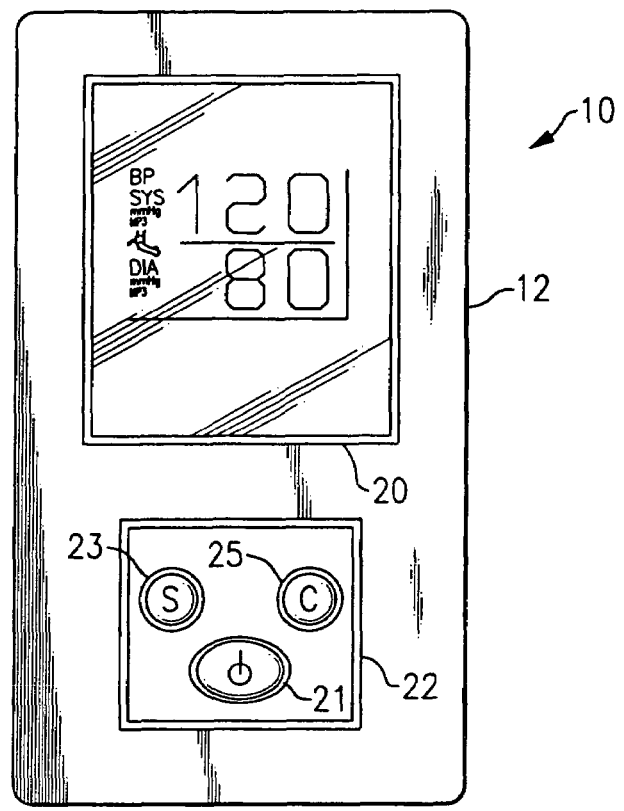
FIG. 1 is a plan view of an embodiment of a blood pressure measurement apparatus in accordance with the present invention.

The present invention will be described herein with reference to an exemplary embodiment of a modular blood pressure measurement apparatus 10 depicted in FIGS. 1 through 6. It is to be understood, however, that this exemplary embodiment of the modular blood pressure measurement apparatus depicted in the drawings is illustrative and not limiting of the present invention.

Figure 2:
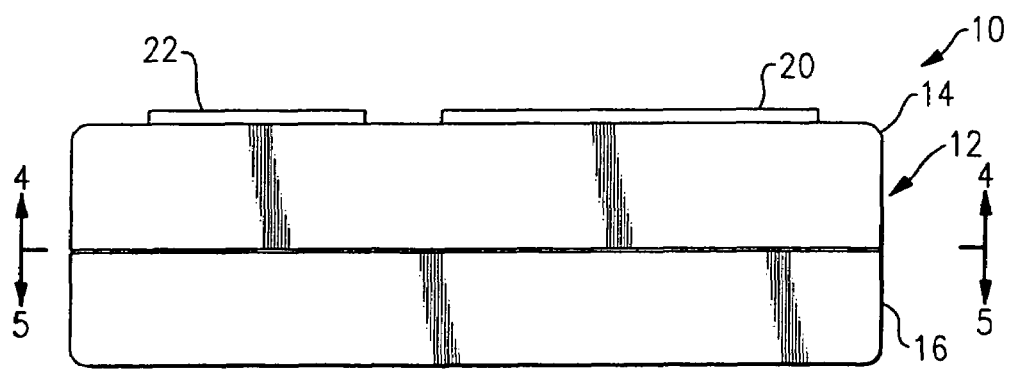
FIG. 2 is a side elevation view of the blood pressure measurement apparatus of FIG. 1.

Referring now to FIGS. 1 and 2 in particular, the blood pressure measurement apparatus 10 includes housing 12 having a first shell 14, which in the exemplary embodiment is an upper shell, and a second shell 16, which in the exemplary embodiment is a lower shell. The upper and lower shells mate to form the housing, and define and enclose an interior space within the housing. A user interface 22, such as, for example, a plurality of input keys 21, 23 and 25 are disposed within corresponding openings in the upper shell 14. The display 20 includes a region for displaying information relating to a blood pressure measurement including the systolic blood pressure (SYS) and the diastolic blood pressure (DIA) measurements in either milligrams of Mercury ("mmHg") or pascals ("kPa") or could also display mean pressure and heart rate. Both the systolic and diastolic blood pressures are displayed as a numeric two or three digit number. For purposes of illustration, the systolic and diastolic blood pressures are shown in FIG. 1 as 120 mmHg and 80 mmHg, respectively. The display 20 may be a LCD display as illustrated in the embodiment shown in the drawings. Key 21 is an on/off switch for selectively powering the apparatus 10 on and off. Key 23 is a start switch for selectively initiating a blood pressure measurement procedure and key 25 is stop switch for selectively canceling a blood pressure measurement procedure.

Figure 3:
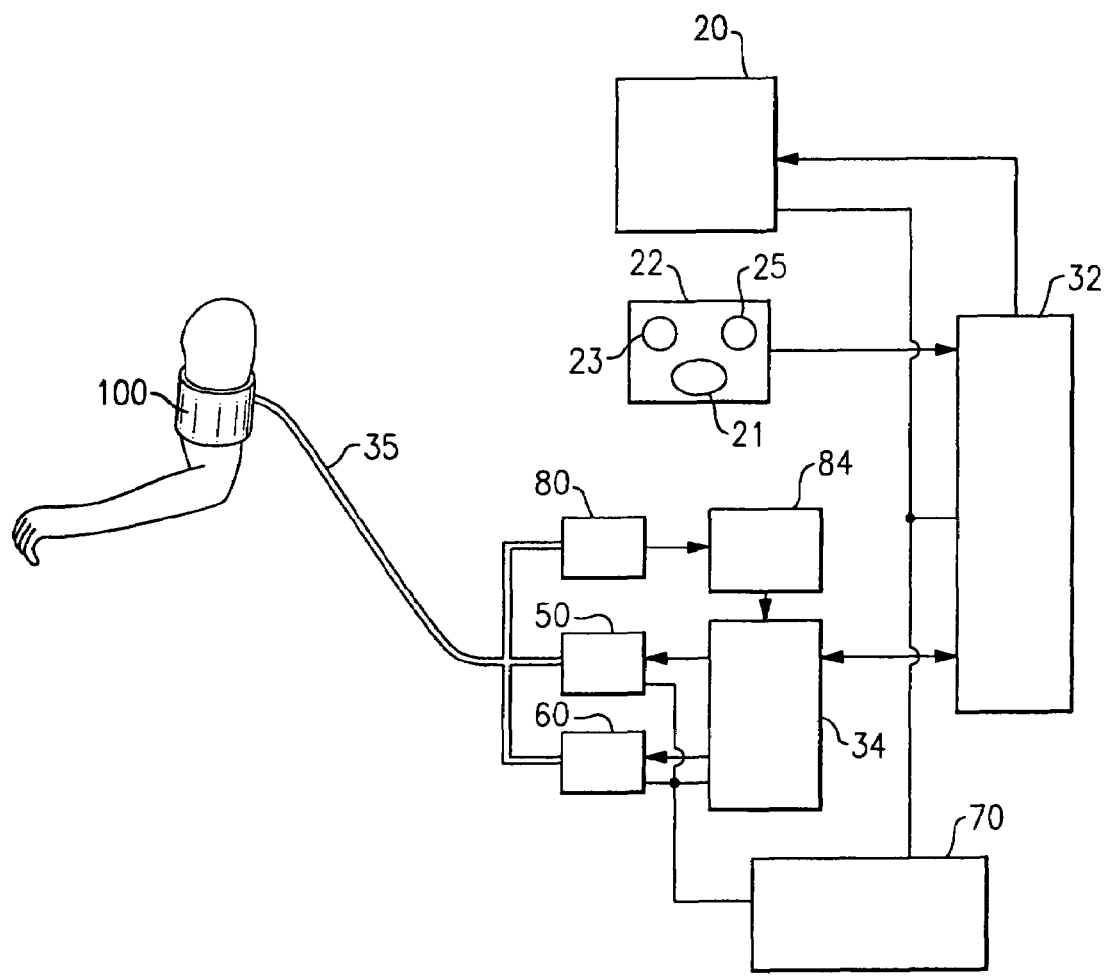
FIG. 3 is a schematic overview illustrating a representative control circuit for the blood pressure measurement apparatus of FIG. 1.
Figure 4:
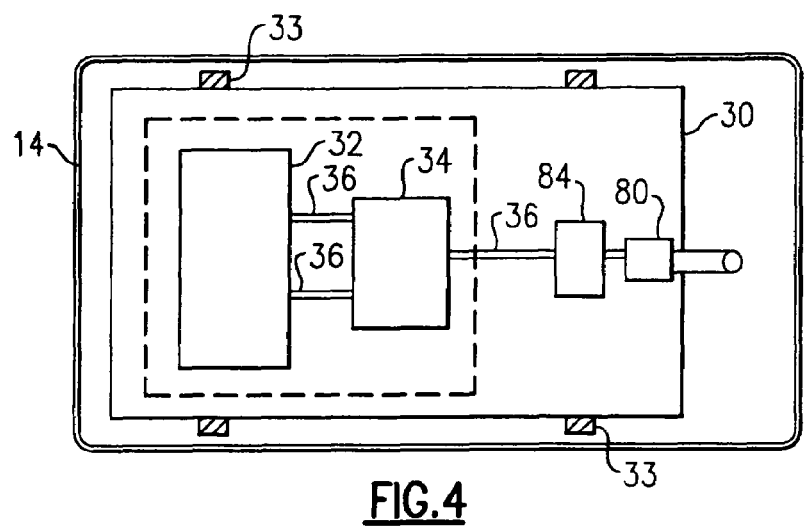
FIG. 4 is a plan view taken along line 4-4 of FIG. 2 showing the components housed within the upper housing of the blood pressure measurement apparatus.

Referring now to FIGS. 3 and 4, the blood pressure measurement apparatus 10 includes a control circuit including microcontroller 32, a non-invasive blood pressure (NIBP) module 34, and a circuit trace 36 disposed on a printed circuit board 30 supported within the upper shell 14. Advantageously, the circuit board 30 may be releaseably mounted within the upper shell 14 thereby constituting a removeable electronics module held in position within the upper shell 14 by any type of releasable mounting means, such as for example, but not limited, conventional flexible snap-lock posts 33. The microcontroller 32, for example a microprocessor, interacts with the display 20 and input keys 21, 23 and 25. The blood pressure measurement apparatus 10 further includes a pump 50, a vent valve 60, a battery power pack 70, and a pressure sensor 80. The pump 50, vent valve 60 and pressure sensor 80, when coupled in pneumatic communication via a conduit 35 to a blood pressure measurement cuff 100 applied to a limb of a patient, operate in a conventional manner in association with the blood pressure cuff 100 to provide for the non-invasive measurement of the systolic and diastolic blood pressures of the patient. The cuff 100 may be any conventional type of blood pressure measurement cuff, such as various "monitor" style cuffs available from Welch Allyn, Inc., headquartered in Skaneateles, N.Y., in sizes for thigh, large adult, adult, small adult, child, small child, and infant. The conduit 35, also commonly referred to as a lumen, may be a rubber tube or a conduit of other suitable material.

The NIBP module 34, which may be a software module incorporated into the microcontroller 32 or may comprise a separate microprocessor coupled in communication with the microprocessor 32, controls operation of the pump 50 and the vent valve 60. The pump 50, which may be a positive displacement pump or other type of inflation pump, is pneumatically coupled to the blood pressure cuff through conduit 35 and is operable to inflate blood pressure cuff 100 in response to a command signal from the NIBP module 34. The vent valve 60 is also pneumatically coupled to the blood pressure cuff 100 through the conduit 35. The vent valve 60, in response to a command signal from the control of the NIBP module 34, provides for selective venting of air from the cuff 100 to deflate the cuff. Additionally, the pressure sensor 80 also communicates pneumatically with the cuff 100 through the conduit 35. The control circuit 30 also includes a sensor electronics module 84 operatively associated with the pressure sensor 80 for receiving the sensed pressure reading from the pressure sensor 80, converting the reading to an electrical signal indicative of the sensed pressure, and transmitting that digital signal indicative of the sensed pressure to the NIBP module 34 or, if desired, directly to the microcontroller. The pressure sensor 80 may comprise a conventional pressure transducer, in which case the sensor electronics module 84 will include an analog-to-digital signal conversion routine.

As in conventional practice, to initiate a blood pressure measurement procedure, the user depresses the on/off switch key 21 to power up the various components of the blood pressure measurement apparatus 10. With the blood pressure measurement cuff 100 in place on the patient, the user depresses the start key 23 to initiate the blood pressure measurement procedure. In response, the NIBP module 34 sends a command signal to the pump 50 to activate the pump 50 to inflate the cuff 100 to a pre-selected desired pressure level for the particular cuff in use. Once the cuff has been inflated to a pre-selected pressure, the NIBP module 34 shuts the pump 50 off and opens the valve 60 to controllably deflate the cuff at a desired rate to enable the patient's diastolic blood pressure, mean blood pressure, systolic blood pressure and pulse rate to be measured automatically in a conventional manner as the cuff deflates. The inflation and deflation rate and timing of the cuff 100 are controlled by the NIBP module 34.

It is to be understood that the particular technique and procedure employed to determine the patient's diastolic and systolic blood pressures is not germane to the invention. The NIBP module 34 of the blood pressure measurement apparatus 10 of the present invention may be preprogrammed to automatically measure the patient's systolic and diastolic blood pressures in various conventional modes, such as in a "Fast BP" mode as the cuff inflates or in a "Step Deflation" mode as the cuff deflates. A detailed discussion and description of the operation of an exemplary embodiment of the NIBP module 32 for blood pressure measurement is presented in co-pending U.S. patent application Ser. No. 10/619,380, filed Jul. 14, 2003, entitled "Motion Measurement in a Blood Pressure Measurement Device", published Feb. 10, 2005, as Patent Application Publication No. US2005/0033188A1, and subject to assignment to the common assignee, which the application is incorporated herein by reference in its entirety.

Figure 5:
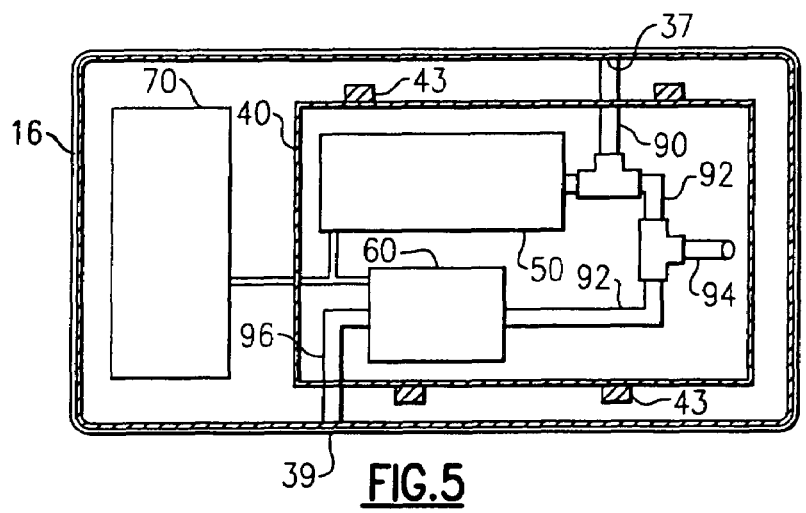
FIG. 5 is a plan view taken along line 5-5 of FIG. 2 showing the components housed within the lower housing of the blood pressure measurement apparatus.

Referring now to FIG. 5, the primary pneumatic components, that is the pump 50 and the vent valve 60, are disposed within a releasable pneumatics module 40 supported within the lower shell 16 of the housing 10. The module 40 may be held in position within the lower shell 16 by any type of releasable mounting means, such as for example, but not limited, conventional flexible snap-lock posts 43. When the replaceable module 40 is properly positioned within the lower shell 16, a first conduit 90 associated with the module 40 is coupled in pneumatic communication with the conduit 35 through the port 37 in the lower housing 16, thereby establishing pneumatic communication between the pump 50 and the inflatable cuff 100. Additionally, within the module 40, a second conduit 92 branches off the first conduit 90 to establish pneumatic communication between the vent valve 60 and the inflatable cuff 100. A third conduit 94 branches off the second conduit 92 to establish pneumatic communication between the pressure sensor 80 and the inflatable cuff 100. A fourth conduit 96 connects the vent value 60 in communication with a vent port 39 in the lower housing 16 through which the vent valve 60 may vent the cuff 100 to atmospheric pressure when it is desired to deflate the cuff 100. In the embodiment of the apparatus depicted in FIG. 5, the battery power pack 70 is disposed in the lower housing 16 externally of and independently of the replaceable module 40. Appropriate electrical connections 72 associated with the power pack 70 are provided to interconnect the power pack 70 with the pump 50 and the vent value 60 within the replaceable module 40, as well as with the various electronic components on the printed circuit board 31. In this embodiment, the pressure sensor 80 is disposed with the upper shell 14, and may be mounted to the printed circuit board 31 or directly to the upper shell 14.

Figure 6:
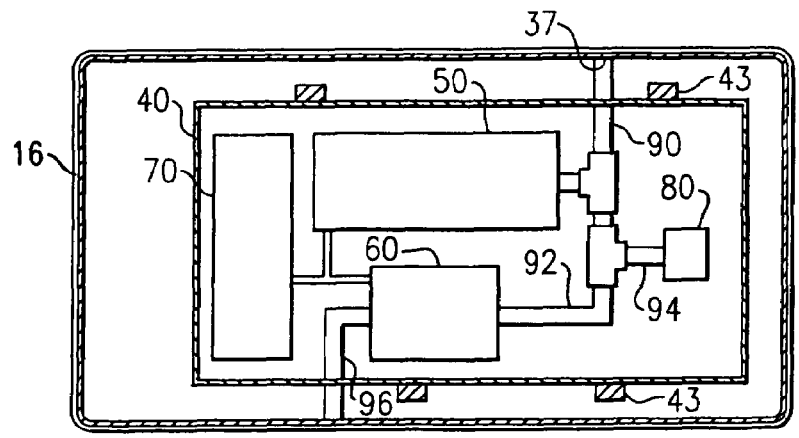
FIG. 6 is a plan view showing an alternate arrangement of components housed within the lower housing of the blood pressure measurement apparatus.

Referring now to FIG. 6, in the embodiment depicted therein, the replaceable module 40 houses not only the primary pneumatic components, i.e. the pump 50 and the vent valve 60, but also the battery power pack 70 and the pressure sensor 80, in this embodiment, when the replaceable module 40 is properly positioned within the lower shell 16, a first conduit 90 associated with the module 40 again is coupled in pneumatic communication with the conduit 35 through the port 37 in the lower housing 16, thereby establishing pneumatic communication between the pump 50 and the inflatable cuff 100. The pressure sensor 80 is connected to the sensor electronics module by means of circuit traces 36. Within the module 40, a second conduit 92 again branches off the first conduit 90 to establish pneumatic communication between the vent valve 60 and the inflatable cuff 100, and a third conduit 94 branches off the second conduit 92 to establish pneumatic communication between the pressure sensor 80 and the inflatable cuff 100. A fourth conduit 96 again connects the vent value 60 in communication with a vent port 39 in the lower housing 16 through which the vent valve 60 may vent the cuff 100 to atmospheric pressure when it is desired to deflate the cuff 100. Appropriate electrical connections 72 associated with the power pack 70 are provided to interconnect the power pack 70 with the pneumatic components commonly housed within the replaceable module 40, as well as with the various electronic components on the printed circuit board 31.

While the present invention has been particularly shown and described with reference to the depicted embodiments as illustrated in the drawing, it will be understood by one skilled in the art that various changes in detail may be effected therein without departing from the spirit and scope of the invention as defined by the claims.

The invention claimed is:

1. A blood pressure measurement apparatus for use in pneumatic communication with a blood pressure measuring cuff; said apparatus comprising:

a housing having an upper casing and a lower casing, the upper and lower casings mating to form the housing and define an interior chamber therein, the upper and lower casings being releasably separable for selective opening of the housing for access to the interior chamber;

a replaceable pneumatics module disposed within the interior chamber and detachably mounted to the lower casing of the housing, said pneumatics module including a pump for selectively inflating the blood pressure measuring cuff and a vent valve for selectively venting the blood pressure measuring cuff;

a replaceable electronics module disposed within the interior chamber and detachably mounted to the pneumatics module and the upper casing of the housing, said electronics module including a display for displaying a blood pressure reading and a control circuit for controlling said pump, said vent valve, and said display, each of said modules including an electrical and pneumatic connector interface, said modules being interconnected via said interface.

2. A blood pressure measurement apparatus as recited in claim 1 wherein said replaceable electronics module further includes a pressure sensor for sensing pressure.

3. A blood pressure measurement apparatus as recited in claim 2 further comprising a power pack operatively associated with and providing electric power to said pump, said valve, said pressure sensor, said display and said control circuit.

4. A blood pressure measurement apparatus as recited in claim 3 wherein said power pack is located in said replaceable pneumatics module.

5. A blood pressure measurement apparatus as recited in claim 1 wherein said replaceable pneumatics module further includes a pressure sensor for sensing pressure.

6. A blood pressure measurement apparatus as recited in claim 5 further comprising a power pack operatively associated with and providing electric power to said pump, said valve, said pressure sensor, said display and said control circuit.

7. A blood pressure measurement apparatus as recited in claim 6 wherein said power pack is located in said replaceable pneumatics module.

* * * * *